(12) United States Patent
Chang et al.

(10) Patent No.: US 10,071,265 B2
(45) Date of Patent: *Sep. 11, 2018

(54) MEDICAL ROBOT

(71) Applicant: Daegu Gyeongbuk Institute of Science and Technology, Daegu (KR)

(72) Inventors: Pyung Hun Chang, Seoul (KR); Gezgin Erkin, Izmir (TR); Seung Ho Kim, Daejeon (KR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 505 days.

This patent is subject to a terminal disclaimer.

(21) Appl. No.: 14/541,104

(22) Filed: Nov. 13, 2014

(65) Prior Publication Data
US 2015/0283406 A1 Oct. 8, 2015

(30) Foreign Application Priority Data

Apr. 7, 2014 (KR) .......................... 10-2014-0041397

(51) Int. Cl.
*A61N 5/10* (2006.01)
*A61B 6/04* (2006.01)
*A61B 6/00* (2006.01)

(52) U.S. Cl.
CPC .............. *A61N 5/1083* (2013.01); *A61B 6/04* (2013.01); *A61B 6/0407* (2013.01);
(Continued)

(58) Field of Classification Search
CPC .. A61N 5/1077; A61N 5/1081; A61N 5/1082; A61N 5/1083; A61N 5/1084;
(Continued)

(56) References Cited

U.S. PATENT DOCUMENTS 4,894,855 A * 1/1990 Kresse ................... A61B 6/032
378/189
5,078,140 A * 1/1992 Kwoh ..................... A61B 34/30
378/20
(Continued)

FOREIGN PATENT DOCUMENTS

JP 2004-283926 A 10/2004
JP 2009-512473 A 3/2009
(Continued)

OTHER PUBLICATIONS

International Search Report for International application No. PCT/KR2014/010921, dated Feb. 13, 2015.
(Continued)

*Primary Examiner* — Allen C. Ho
(74) *Attorney, Agent, or Firm* — Marshall, Gerstein & Borun LLP

(57) ABSTRACT

A medical robot includes a bed on which an object is to be disposed, and a robot arm unit disposed above or below the bed, and including an emitting member movable within a trajectory on a sphere having a center at which a target point is disposed, wherein the bed and the robot arm unit may move relatively in a vertical or horizontal direction, and the object may be repositioned to the target point by relatively moving the bed and the robot arm unit in the vertical or horizontal direction, and the emitting member may move to face the target point.

17 Claims, 6 Drawing Sheets

(52) U.S. Cl.
CPC .......... *A61B 6/0457* (2013.01); *A61B 6/4429* (2013.01); *A61B 6/4458* (2013.01); *A61B 6/4464* (2013.01); *A61N 5/1077* (2013.01); *A61N 5/1081* (2013.01); *A61N 5/1082* (2013.01); *A61N 5/1084* (2013.01)

(58) Field of Classification Search
CPC ....... A61B 6/04; A61B 6/0407; A61B 6/0457; A61B 6/4429; A61B 6/4458
USPC ................................... 378/65, 68, 197–198
See application file for complete search history.

(56) References Cited

U.S. PATENT DOCUMENTS

| | | | | |
|---|---|---|---|---|
| 5,549,439 A * | 8/1996 | Ploem | ............... | A61B 6/102 378/204 |
| 6,155,713 A * | 12/2000 | Watanabe | ............ | A61B 6/4441 378/197 |
| 6,200,024 B1 * | 3/2001 | Negrelli | ............... | A61B 6/4458 378/197 |
| 6,213,638 B1 * | 4/2001 | Rattner | ............... | A61B 6/4441 378/198 |
| 6,338,714 B1 * | 1/2002 | Krause | ................ | A61G 12/004 128/897 |
| 6,435,715 B1 * | 8/2002 | Betz | .................... | A61B 6/4458 378/197 |
| 6,530,688 B1 * | 3/2003 | Müller | ............... | B25J 17/0266 378/197 |
| 6,582,121 B2 * | 6/2003 | Crain | .................... | A61B 6/107 378/189 |
| 6,590,958 B2 * | 7/2003 | Barber | .................. | A61B 6/107 378/196 |
| 6,592,259 B2 * | 7/2003 | Crain | .................... | A61B 6/107 378/196 |
| 6,614,871 B1 * | 9/2003 | Kobiki | ................. | A61B 6/035 250/522.1 |
| 6,637,936 B2 * | 10/2003 | Crain | .................... | A61B 6/107 378/162 |
| 6,644,852 B2 * | 11/2003 | Crain | .................... | A61B 6/107 378/193 |
| 6,826,254 B2 * | 11/2004 | Mihara | ................. | A61N 5/10 250/492.3 |
| 6,869,217 B2 * | 3/2005 | Rasche | ............... | A61B 6/4441 378/197 |
| 6,888,919 B2 * | 5/2005 | Graf | .................... | A61N 5/1049 378/197 |
| 6,977,987 B2 * | 12/2005 | Yamashita | ............ | A61N 5/10 378/64 |
| 7,081,700 B2 * | 7/2006 | Okumura | .................. | B25J 7/00 310/323.17 |
| 7,085,347 B2 * | 8/2006 | Mihara | .................... | A61N 5/10 378/197 |
| 7,188,999 B2 * | 3/2007 | Mihara | .................... | A61N 5/10 378/17 |
| 7,266,176 B2 * | 9/2007 | Allison | ................ | A61N 5/1031 378/205 |
| 7,330,578 B2 * | 2/2008 | Wang | ..................... | G06T 15/08 345/419 |
| 7,362,848 B2 * | 4/2008 | Saracen | ............... | A61N 5/1038 378/64 |
| 7,401,977 B2 * | 7/2008 | Graumann | ........... | A61B 6/4441 378/197 |
| 7,441,953 B2 * | 10/2008 | Banks | .................. | A61B 5/1038 378/197 |
| 7,500,784 B2 * | 3/2009 | Grebner | ............... | A61B 6/4441 378/193 |
| 7,508,913 B2 * | 3/2009 | Boese | ................... | A61B 6/12 378/205 |
| 7,590,219 B2 * | 9/2009 | Maurer, Jr. | ........... | A61N 5/103 378/145 |
| 7,594,751 B2 * | 9/2009 | Grebner | ............... | A61B 6/4014 378/196 |
| 7,623,679 B2 * | 11/2009 | West | .................... | A61N 5/1031 382/103 |
| 7,656,998 B2 * | 2/2010 | Main | .................... | A61N 5/1049 378/19 |
| 7,713,205 B2 * | 5/2010 | Fu | ............................. | A61B 8/08 600/437 |
| 7,724,870 B2 * | 5/2010 | Maltz | .................... | A61B 6/025 378/189 |
| 7,801,349 B2 * | 9/2010 | Wang | .................... | A61N 5/1031 378/65 |
| 7,831,073 B2 * | 11/2010 | Fu | ........................ | A61N 5/1049 382/128 |
| 7,860,550 B2 * | 12/2010 | Saracen | ............... | A61B 6/0457 378/209 |
| 7,889,902 B2 * | 2/2011 | Zhang | .................... | G06T 15/08 345/502 |
| 7,891,935 B2 * | 2/2011 | Kremerman | ............. | B25J 9/042 414/744.5 |
| 7,905,658 B2 * | 3/2011 | Groß | .................... | 378/193 |
| 7,934,869 B2 * | 5/2011 | Ivanov | ................... | A61N 5/1049 378/20 |
| 7,938,579 B2 * | 5/2011 | Groß | .................... | A61B 6/4458 378/197 |
| 7,945,021 B2 * | 5/2011 | Shapiro | .................. | A61B 6/032 378/19 |
| 7,972,061 B2 * | 7/2011 | Groß | .................... | A61B 6/4441 378/197 |
| 7,978,817 B2 * | 7/2011 | Rietzel | ................. | A61N 5/1049 378/197 |
| 7,985,023 B2 * | 7/2011 | Groß | .................... | A61B 6/4441 378/194 |
| 7,988,357 B2 * | 8/2011 | Hornung | ............. | A61B 6/4233 378/197 |
| 8,011,828 B2 * | 9/2011 | Beimler | .................. | B25J 9/104 378/189 |
| 8,064,642 B2 * | 11/2011 | Sheng | .................... | A61B 5/1127 382/103 |
| 8,113,711 B2 * | 2/2012 | Beimler | .................. | B25J 9/104 378/189 |
| 8,126,114 B2 * | 2/2012 | Naylor | ................. | A61N 5/1049 378/65 |
| 8,142,420 B2 * | 3/2012 | Schena | ................. | A61B 34/70 606/1 |
| 8,160,205 B2 * | 4/2012 | Saracen | ................. | A61B 6/0457 378/35 |
| 8,162,926 B2 * | 4/2012 | Schena | ............. | A61B 19/2203 606/1 |
| 8,167,872 B2 * | 5/2012 | Schena | ................. | A61B 34/70 606/1 |
| 8,167,873 B2 * | 5/2012 | Schena | ................. | B25J 17/0266 606/1 |
| 8,180,020 B2 * | 5/2012 | Kilby | .................... | A61N 5/1031 378/65 |
| 8,295,435 B2 * | 10/2012 | Wang | ....................... | A61N 5/10 378/65 |
| 8,303,575 B2 * | 11/2012 | Rodriguez Y Baena | .................... | A61B 34/70 606/1 |
| 8,315,356 B2 * | 11/2012 | Core | .................... | A61N 5/1049 378/205 |
| 8,320,517 B2 * | 11/2012 | Dennerlein | ............ | A61B 6/032 378/4 |
| 8,406,851 B2 * | 3/2013 | West | .................... | A61N 5/1049 600/411 |
| 8,459,867 B2 * | 6/2013 | Muller | ................. | A61B 6/4464 378/196 |
| 8,469,945 B2 * | 6/2013 | Schena | ................. | B25J 17/0258 606/1 |
| 8,534,915 B2 * | 9/2013 | Maschke | ............. | A61B 6/4411 378/196 |
| 8,606,348 B2 * | 12/2013 | Maschke | ............. | A61B 6/505 600/425 |
| 8,611,495 B2 * | 12/2013 | Maschke | ............. | A61B 6/4014 378/197 |
| 8,655,429 B2 * | 2/2014 | Kuduvalli | ........... | A61N 5/1049 250/491.1 |

(56) References Cited

U.S. PATENT DOCUMENTS

| | | | | |
|---|---|---|---|---|
| 8,917,813 B2* | 12/2014 | Maurer, Jr. | ............... | A61N 5/10 378/197 |
| 8,944,680 B2* | 2/2015 | Graumann | ........... | A61B 6/4452 250/491.1 |
| 8,989,846 B2* | 3/2015 | Kuduvalli | ................ | A61B 6/00 378/181 |
| 9,016,942 B2* | 4/2015 | Guo | ..................... | A61B 6/4458 378/204 |
| 9,107,633 B2* | 8/2015 | Muller | ................. | A61B 6/0407 |
| 9,227,083 B2* | 1/2016 | Hastenteufel | ............ | A61N 5/10 |
| 9,248,571 B2* | 2/2016 | Amberg | ............. | B25J 9/1664 |
| 9,415,240 B2* | 8/2016 | Jordan | ................. | A61B 6/4035 |
| 9,625,581 B2* | 4/2017 | Chang | ................. | B29C 67/0085 |
| 9,855,446 B2* | 1/2018 | Chang | ................. | A61N 5/1084 |
| 9,895,559 B2* | 2/2018 | Chang | ................. | A61N 5/1083 |
| 2010/0069920 A1 | 3/2010 | Naylor et al. | | |
| 2010/0104068 A1 | 4/2010 | Kilby et al. | | |
| 2012/0045308 A1 | 2/2012 | Kremerman | | |
| 2013/0223597 A1 | 8/2013 | Graumann | | |

FOREIGN PATENT DOCUMENTS

| | | |
|---|---|---|
| KR | 20100119106 A | 11/2010 |
| KR | 10-1304280 B1 | 9/2013 |
| KR | 10-1339009 B1 | 12/2013 |
| KR | 10-20130134206 A | 12/2013 |
| KR | 20130134200 A | 12/2013 |
| WO | WO-2003/018131 A1 | 3/2003 |
| WO | WO-2010/030463 A1 | 3/2010 |

OTHER PUBLICATIONS

Supplementary European Search Report for European Patent Application No. 14866815, dated Aug. 3, 2016.

Office Action issued in Chinese Patent Application No. 201480023028.5, dated Dec. 2, 2016.

* cited by examiner

MEDICAL ROBOT

CROSS-REFERENCE TO RELATED APPLICATION

This application claims the benefit of Korean Patent Application No. 10-2014-0041397, filed on Apr. 7, 2014, in the Korean Intellectual Property Office, the disclosure of which is incorporated herein by reference.

BACKGROUND

1. Field of the Invention

Embodiments of the present invention relate to a medical robot, and more particularly, to a medical robot that may be aimed at a treatment area accurately and rapidly.

2. Description of the Related Art

Radiation therapy is a form of treatment to kill cancer cells using high-energy radiation. Radiation refers to a material mediating propagation or a phenomenon of energy propagating through a space, and an X-ray is a typical example of the radiation.

Radiation therapy is one of the three most prevalent cancer treatments, in company with surgery and chemotherapy. In general, radiation therapy may not require hospitalization, take a few to about 30 minutes per day, and be painless during treatment.

As radiation therapy apparatuses, X-Knife (Radionics, U.S.A.), Novalis Tx (BrainLAB, Germany), Peacok (NO-MOS Corp., U.S.A.), Trilogy (Varian Medical System, U.S.A.), and CyberKnife (Accuray Inc., U.S.A.) are known. Many of the radiation therapy apparatuses are evolving to reduce an error occurring during treatment and increase an accuracy based on technology of Image Guided Radiotherapy (IGRT) and a linear accelerator.

CyberKnife is a high-precision stereotactic radiation therapy exclusive apparatus that may intensively irradiate a tumor portion in various directions by providing a small linear accelerator to a robot arm freely moving with six joints.

CyberKnife may provide a precise treatment by tracking coordinates of a gold marker inserted into a body and a skeleton image using real-time image guided technology, without an invasive fixing device. In addition, contrary to Gamma Knife used to treat brain tumors, CyberKnife may be used to treat cancer throughout a human body. Further, CyberKnite may be used for fractionated radiation therapy administered a few times, rather than once.

Recently, research is being conducted on CyberKnife. For example, Korean Patent Application No. 2009-0038051, filed on Apr. 30, 2009, discloses "System for radiotherapy planning information viewer".

SUMMARY

An aspect of the present invention provides a medical robot that may be aimed at a target point rapidly and accurately through relative movements of a robot arm unit and a bed.

Another aspect of the present invention also provides a medical robot that may increase a directivity with respect to a target point through easy control, thereby reducing a treatment or surgery time.

Still another aspect of the present invention also provides a medical robot that may reduce an overall weight by reducing a number of drive members through a compact design.

Yet another aspect of the present invention also provides a medical robot that may prevent a mutual collision between robot arm units by rotating a plurality of robot arm units independently and incoherently.

Further another aspect of the present invention also provides a medical robot that may efficiently enable an emitting member to be aimed at an object by adjusting a position of a bed.

According to an aspect of the present invention, there is provided a medical robot including a bed on which an object is to be disposed, and a robot arm unit disposed above or below the bed, and including an emitting member movable within a trajectory on a sphere having a center at which a target point is disposed. The bed and the robot arm unit may move relatively in a vertical or horizontal direction, and the object may be repositioned to the target point by relatively moving the bed and the robot arm unit in the vertical or horizontal direction, and the emitting member may move to face the target point.

The robot arm unit may include an upper robot arm to rotate above the bed, and a lower robot arm to rotate below the bed. An emitting member of the upper robot arm and an emitting member of the lower robot arm may be disposed to face an identical target point.

The upper robot arm and the lower robot may be disposed within trajectories on spheres having an identical center.

The robot arm unit may include a plurality of link members and a plurality of drive members, the plurality of link members may be disposed on concentric spheres having an identical center, and extension lines of axes of the drive members may be positioned at the center.

The center of the concentric spheres may match the target point.

The robot arm unit may include a first central member, a first link member to rotate on a longitudinal axis of the first central member, a first drive member disposed at one end of the first link member to transmit a torque to the first link member, a second link member connected to another end of the first link member to rotate on a first axis, and a second drive member disposed between the first link member and the second link member to transmit a torque to the second link member.

The robot arm unit may further include a third link member connected to a portion of the first central member, the portion differing from a portion to which the first link member is connected, to rotate on the longitudinal axis of the first central member, a third drive member disposed at one end of the third link member to transmit a torque to the third link member, a fourth link member connected to another end of the third link member to rotate on a second axis, and a fourth drive member disposed between the third link member and the fourth link member to transmit a torque to the fourth link member.

The robot arm unit may further include a second central member disposed on an axis identical to the longitudinal axis of the first central member and spaced apart from the center by a distance corresponding to a distance between the first central member and the center, a fifth link member to rotate on a longitudinal axis of the second central member, a fifth drive member disposed at one end of the fifth link member to transmit a torque to the fifth link member, a sixth link member connected to another end of the fifth link member to rotate on a third axis, and a sixth drive member disposed between the fifth link member and the sixth link member to transmit a torque to the sixth link member.

The robot arm unit may further include a seventh link member connected to a portion of the second central member, the portion differing from a portion to which the fifth link member is connected, to rotate on the longitudinal axis of the second central member, a seventh drive member disposed at one end of the seventh link member to transmit a torque to the seventh link member, an eighth link member connected to another end of the seventh link member to rotate on a fourth axis, and an eighth drive member disposed between the seventh link member and the eighth link member to transmit a torque to the eighth link member.

The longitudinal axis of the first central member, the longitudinal axis of the second central member, the first axis, the second axis, the third axis, and the fourth axis may be positioned at the center.

The first axis, the second axis, the third axis, and the fourth axis may be formed to be perpendicular to tangential directions of end portions of the first link member, the second link member, the third link member, the fourth link member, the fifth link member, the sixth link member, the seventh link member, and the eighth link member.

The first link member and the second link member may be disposed farther away from the center than the third link member and the fourth link member, and the fifth link member and the sixth link member may be disposed farther away from the center than the seventh link member and the eighth link member.

When the third link member is disposed between the first link member and the second link member, lengths of the third link member and the fourth link member may be shorter than a length of the first link member.

The third link member and the fourth link member may be disposed closer to the center than the second link member, and the fourth link member may be disposed closer to the center than the third link member.

When the seventh link member is disposed between the fifth link member and the sixth link member, lengths of the seventh link member and the eighth link member may be shorter than a length of the fifth link member.

The seventh link member and the eighth link member may be disposed closer to the center than the sixth link member, and the eighth link member may be disposed closer to the center than the seventh link member.

The robot arm unit may further include emitting members provided at respective end portions of the second link member, the fourth link member, the sixth link member, and the eighth link member to face the center.

The emitting members may be disposed to be perpendicular to tangential directions of the end portions of the second link member, the fourth link member, the sixth link member, and the eighth link member.

The medical robot may further include a position adjustment element to adjust a position of the bed.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Figure 1:
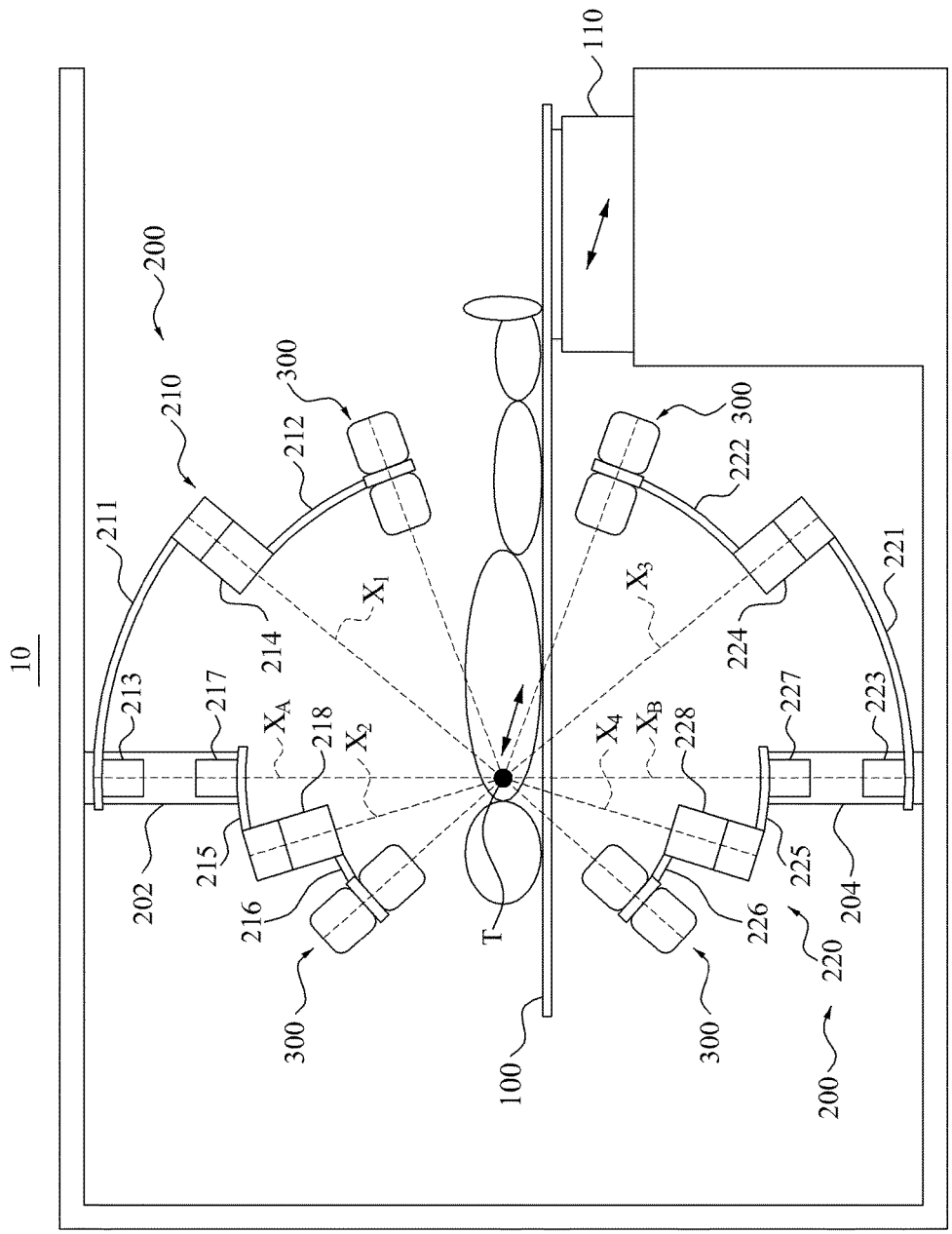
FIG. 1 illustrates a medical robot according to an embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

Figure 2:
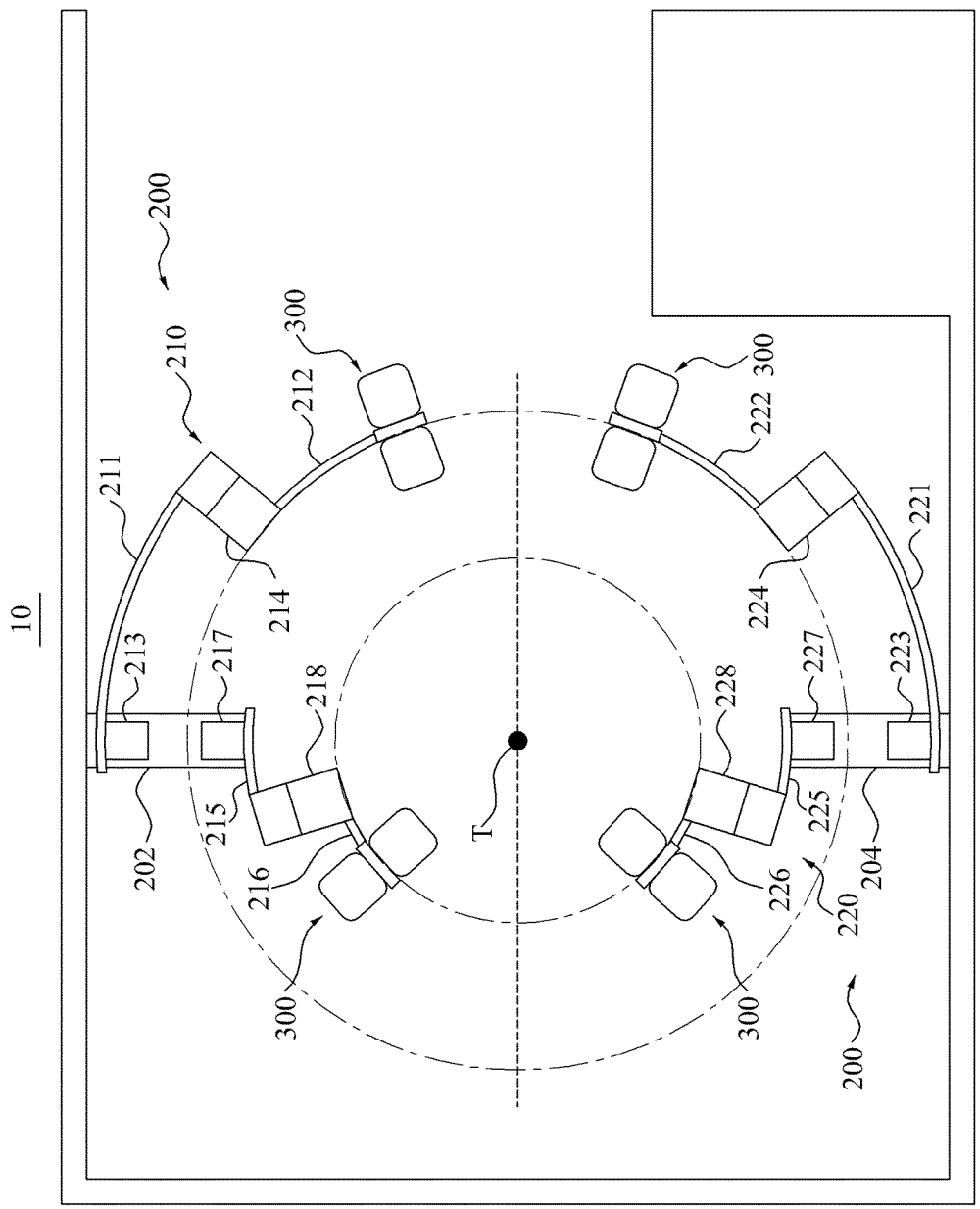
FIG. 2 illustrates a disposition of a robot arm unit in a medical robot according to an embodiment of the present invention.
Figure 3:
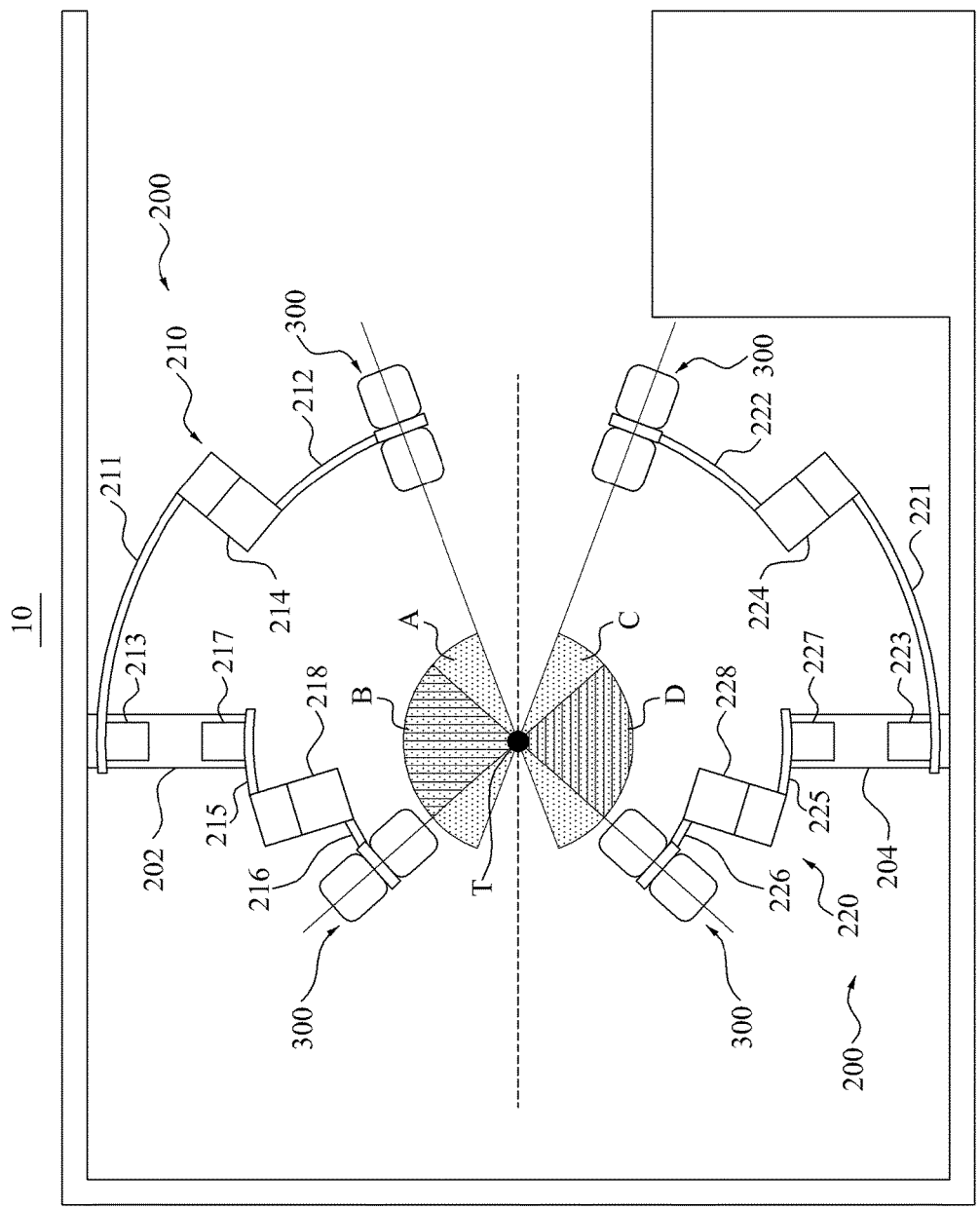
FIG. 3 illustrates a radiation range of emitting members of a medical robot according to an embodiment of the present invention.
Figure 4:
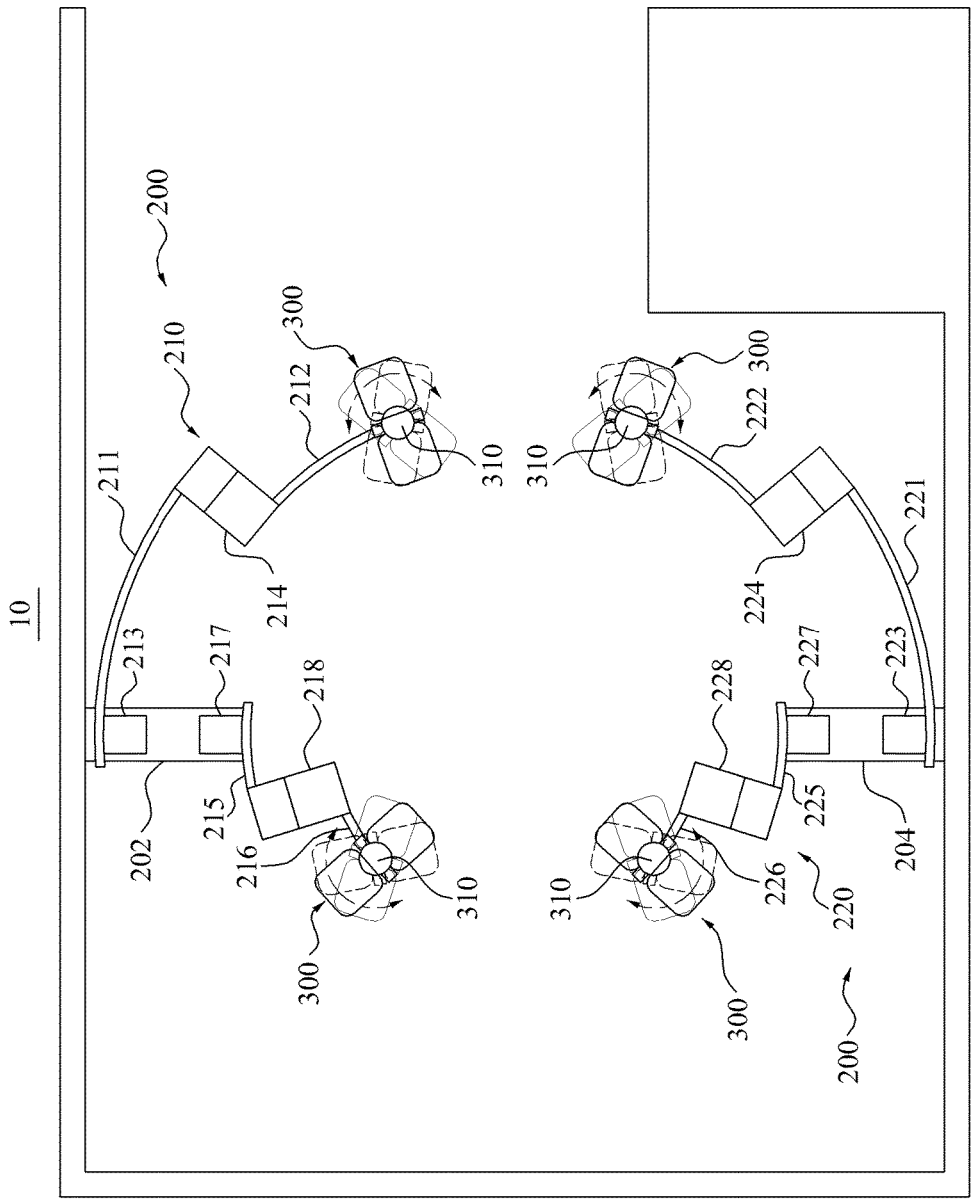
FIG. 4 illustrates angle adjustment elements disposed in a medical robot according to an embodiment of the present invention.

FIG. 1 illustrates a medical robot 10 according to an embodiment of the present invention, FIG. 2 illustrates a disposition of a robot arm unit 200 in the medical robot 10 according to an embodiment of the present invention, FIG. 3 illustrates a radiation range of emitting members 300 of the medical robot 10 according to an embodiment of the present invention, and FIG. 4 illustrates angle adjustment elements 310 disposed in the medical robot 10 according to an embodiment of the present invention.

Referring to FIG. 1, the medical robot 10 may include a bed 100 and a robot arm unit 200.

An object may be disposed on the bed 100. The object may be, for example, a patient.

When the medical robot 10 is used as a cyberknife, the object may be a cancer patient requiring radiation therapy or a tumor removing surgery. In this example, a target point T may be a treatment or surgery area, for example, a position of a tumor.

A position adjustment element 110 may be disposed at the bed 100 to adjust a position of the bed 100.

As shown in FIG. 1, when the position adjustment element 110 moves in a direction of an arrow, the bed 100 may also move in the direction of the arrow.

The position of the bed 100 or the object may be freely adjusted and thus, the target point T may be repositioned.

In detail, the bed 100 may move in a direction vertical or horizontal to the ground.

Accordingly, the bed 100 and the robot arm unit 200 may move relatively in the vertical or horizontal direction.

When the bed 100 is fixed, the position of the object may be fixed. By moving the robot arm unit 200, an irradiation position of an emitting member 300 or a position at which radiation is emitted from the emitting member 300 may be moved relatively with respect to the bed 100.

The object may be repositioned to the target point T by relatively moving the bed 100 with respect to the robot arm unit 200 through the position adjustment element 110, and the emitting member 300 may move to face the target point T.

Thus, the emitting member 300 provided at the robot arm unit 200 may be efficiently aimed at the target point T of the object disposed on the bed 100, which will be described in detail hereinafter.

The robot arm unit 200 may be disposed above or below the bed 100.

The robot arm unit 200 may include an upper robot arm 210 and a lower robot arm 220. The emitting member 300 may be provided at an end portion of each of the upper robot arm 210 and the lower robot arm 220.

In this example, radiation may be emitted from the emitting member 300, and the radiation may be emitted or irradiated toward the target point T of the object.

Referring to FIG. 2, the upper robot arm 210 and the lower robot arm 220 may be disposed within trajectories on spheres having an identical center, for example, the identical target point T.

The emitting member 300 of the upper robot arm 210 and the emitting member 300 of the lower robot arm 220 may move in response to rotation of the upper robot arm 210 and the lower robot arm 220. Thus, the emitting members 300 may move along spherical trajectories of the upper robot arm 210 and the lower robot arm 220. The emitting members 300 may be disposed to face the identical target point T.

Accordingly, radiation emitted from the emitting member 300 provided on the upper robot arm 210 and radiation emitted from the emitting member 300 provided on the lower robot arm 220 may be concentrated on a single singular point. The emitting members 300 may be easily aimed at a treatment area.

The upper robot arm 210 and the lower robot arm 220 may be disposed to be spaced apart from each other based on the bed 100.

Through such a disposition of the upper robot arm 210 and the lower robot arm 220, the upper robot arm 210 and the lower robot arm 220 may operate incoherently, and a mutual collision between the upper robot arm 210 and the lower robot arm 220 may be prevented.

The upper robot arm 210 and the lower robot arm 220 may respectively include a plurality of link members and a plurality of drive members.

For example, the upper robot arm 210 may include a first link member 211, a second link member 212, a third link member 215, and a fourth link member 216.

The first link member 211 may be provided at a first central member 202 to rotate on a longitudinal axis $X_A$ of the first central member 202.

The first central member 202 may be disposed in a vertical direction on an inner side of a frame provided on an outer side of the medical robot 10.

The first link member 211 may be disposed on a sphere having a center at the target point T, and provided in a form of an arc.

The first link member 211 may have a longer length than the second link member 212, the third link member 215, and the fourth link member 216, and be disposed farthest away from the target point T.

The second link member 212 may be connected to another end of the first link member 211.

The second link member 212 may rotate based on a first axis $X_1$.

The first axis $X_1$ may be angled with respect to the longitudinal axis $X_A$ of the first central member 202.

The third link member 215 may be connected to a portion of the first central member 202, the portion differing from a portion to which the first link member 211 is connected.

The third link member 215 may rotate on the longitudinal axis $X_A$ of the first central member 202.

For example, the first link member 211 may be connected to an upper portion of the first central member 202, and the third link member 215 may be connected to a lower portion of the first central member 202.

The fourth link member 216 may be connected to another end of the third link member 215.

The fourth link member 216 may rotate on a second axis $X_2$.

The second axis $X_2$ may be angled with respect to the longitudinal axis $X_A$ of the first central member 202.

The upper robot arm 210 may further include a first drive member 213, a second drive member 214, a third drive member 217, and a fourth drive member 218.

The first drive member 213 may be included in the first central member 202. Although not illustrated in detail, the first central member 202 may include a space in which the first drive member 213 is to be disposed.

The first drive member 213 may transmit a torque to the first link member 211.

The second drive member 214 may transmit a torque to the second link member 212. The second drive member 214 may be disposed to face the target point T along the first axis $X_1$.

Similar to the first drive member 213, the third drive member 217 may be included in the first central member 202. The first central member 202 may include a space in which the third drive member 217 is to be disposed.

The third drive member 217 may transmit a torque to the third link member 215.

The first drive member 213 and the third drive member 217 may be provided integrally or separately. For example, when the first drive member 213 and the third drive member 217 are provided separately, the first link member 211 and the third link member 215 may rotate in different directions or at different velocities.

The fourth drive member 218 may transmit a torque to the fourth link member 216. The fourth drive member 218 may be disposed to face the target point T along the second axis $X_2$.

In this example, extension lines of the longitudinal axis $X_A$ of the first central member 202, the first axis $X_1$, and the second axis $X_2$ may be positioned at the target point T.

The emitting member 300 provided at the second link member 212 and the emitting member 300 provided at the fourth link member 216 may be provided in a vertical direction with respect to the second link member 212 and the fourth link member 216, and disposed to face the target point T.

In addition to the extension lines of the longitudinal axis $X_A$ of the first central member 202, the first axis $X_1$, and the second axis $X_2$, the emitting members 300 and the drive members 213, 214, 217, and 218 may also be disposed to face the target point T. Thus, radiations may be emitted or irradiated from the emitting members 300 toward the target point T.

The lower robot arm 220 may include a fifth link member 221, a sixth link member 222, a seventh link member 225, and an eighth link member 226.

The fifth link member 221 may rotate on a longitudinal axis $X_B$ of a second central member 204.

The second central member 204 may be disposed in a vertical direction on the inner side of the frame provided on the outer side of the medical robot 10.

The first central member 202 and the second central member 204 may be provided on an identical axis. The second central member 204 may be spaced apart from the target point T by a distance corresponding to a distance between the first central member 202 and the target point T.

The fifth link member 221 may be disposed on a sphere having a center at the target point T, and provided in a form of an arc.

The sixth link member 222 may be connected to another end of the fifth link member 221.

The sixth link member 222 may rotate on a third axis $X_3$.

The third axis $X_3$ may be angled with respect to the longitudinal axis $X_B$ of the second central member 204.

The seventh link member 225 may be connected to a portion of the second central member 204, the portion differing from a portion to which the fifth link member 221 is connected.

The seventh link member 225 may rotate on the longitudinal axis $X_B$ of the second central member 204.

For example, the fifth link member 221 may be connected to a lower portion of the second central member 204, and the seventh link member 225 may be connected to an upper portion of the second central member 204.

The eighth link member 226 may be connected to another end of the seventh link member 225.

The eighth link member 226 may rotate on a fourth axis $X_4$.

The fourth axis $X_4$ may be angled with respect to the longitudinal axis $X_B$ of the second central member 204.

The lower robot arm 220 may further include a fifth drive member 223, a sixth drive member 224, a seventh drive member 227, and an eighth drive member 228.

The fifth drive member 223 may be included in the second central member 204. The fifth drive member 223 may transmit a torque to the fifth link member 221.

The sixth drive member 224 may transmit a torque to the sixth link member 222. The sixth drive member 224 may be disposed to face the target point T along the third axis $X_3$.

Similar to the fifth drive member 223, the seventh drive member 227 may be included in the second central member 204. The seventh drive member 227 may transmit a torque to the seventh link member 225.

The fifth drive member 223 and the seventh drive member 227 may be provided integrally or separately. For example, when the fifth drive member 223 and the seventh drive member 227 are provided separately, the fifth link member 221 and the seventh link member 225 may rotate in different directions or at different velocities.

The eighth drive member 228 may transmit a torque to the eighth link member 226. The eighth drive member 228 may be disposed to face the target point T along the fourth axis $X_4$.

In this example, extension lines of the longitudinal axis $X_B$ of the second central member 204, the third axis $X_3$, and the fourth axis $X_4$ may be positioned at the target point T.

The emitting member 300 provided at the sixth link member 222 and the emitting member 300 provided at the eighth link member 226 may be provided in a vertical direction with respect to the sixth link member 222 and the eighth link member 226, and disposed to face the target point T.

In addition to the extension lines of the longitudinal axis $X_B$ of the second central member 204, the third axis $X_3$, and the fourth axis $X_4$, the emitting members 300 and the drive members 223, 224, 227, and 228 may also be disposed to face the target point T. Thus, radiations may be emitted or irradiated from the emitting members 300 toward the target point T.

In the drawings, the upper robot arm 210 and the lower robot arm 220 are provided in similar or identical forms. However, the forms of the upper robot arm 210 and the lower robot arm 220 are not limited thereto. The upper robot arm 210 and the lower robot arm 220 may be provided in any form in which the emitting member 300 provided at the upper robot arm 210 and the emitting member 300 provided at the lower robot arm 220 are disposed to face the identical target point T.

To prevent a mutual collision when the plurality of link members 211, 212, 215, 216, 221, 222, 225, and 226 of the upper robot arm 210 and the lower robot arm 220 rotates simultaneously, the plurality of link members 211, 212, 215, 216, 221, 222, 225, and 226 may be disposed as follows.

The first link member 211 and the second link member 212 may be disposed farther away from the target point T than the third link member 215 and the fourth link member 216, and the fifth link member 221 and the sixth link member 222 may be disposed farther away from the target point T than the seventh link member 225 and the eighth link member 226.

When the third link member 215 is disposed between the first link member 211 and the second link member 212, the length of the third link member 215 may be shorter than the length of the first link member 211, and the fourth link member 216 may be disposed closer to the target point T than the second link member 212.

When the seventh link member 225 is disposed between the fifth link member 221 and the sixth link member 222, the length of the seventh link member 225 may be shorter than the length of the fifth link member 221, and the eighth link member 226 may be disposed closer to the target point T than the sixth link member 222.

The upper robot arm 210 may emit radiation above the bed 100, and the lower robot arm 220 may emit radiation below the bed 100.

Referring to FIG. 3, the upper robot arm 210 may emit radiation within an area A and an area B, and the lower robot arm 220 may emit radiation within an area C and an area D.

The area A indicates a range of radiation emitted from the emitting member 300 by means of the first link member 211 and the second link member 212, the area B indicates a range of radiation emitted from the emitting member 300 by means of the third link member 215 and the fourth link member 216, the area C indicates a range of radiation emitted from the emitting member 300 by means of the fifth link member 221 and the sixth link member 222, and the area D indicates a range of radiation emitted from the emitting member 300 by means of the seventh link member 225 and the eighth link member 226.

The area A, the area B, the area C, and the area D may be positioned at the target point T, and the upper robot arm 210 and the lower robot arm 220 may emit radiations toward different areas.

As described above, the upper robot arm 210 may have a spherical trajectory of rotation above the bed 100, and the lower robot arm 220 may have a spherical trajectory of rotation below the bed 100. Thus, the upper robot arm 210 and the second robot arm 220 may have independent motions with respect to each other, thereby preventing mutual interference.

Referring to FIG. 4, the angle adjustment elements 310 may be provided at the emitting members 300 or end portions of the second link member 212, the fourth link member 216, the sixth link member 222, and the eighth link member 226 to move the emitting members 300 at a relatively small angle.

Through the angle adjustment elements 310, the medical robot 10 may more efficiently operate the emitting members 300 to be aimed at the target point T. For example, the angle adjustment elements 310 may be useful when a minute angle adjustment is required after the emitting members 300 are aimed at the target point T by means of the drive members 213, 214, 217, 218, 223, 224, 227, and 228.

All axes of the drive members 213, 214, 217, 218, 223, 224, 227, and 228 may face the target point T. Thus, the emitting members 300 may be continuously aimed at the target point T while the link members 211, 212, 215, 216, 221, 222, 225, and 226 are rotating. The foregoing may be achieved based on a structural disposition of the link members 211, 212, 215, 216, 221, 222, 225, and 226 and the drive members 213, 214, 217, 218, 223, 224, 227, and 228.

In particular, radiations may be emitted in a state in which the link members 211, 212, 215, 216, 221, 222, 225, and 226 of the robot arms 210 and 220 are stationary. Thus, radiations may not be emitted while the link members 211, 212, 215, 216, 221, 222, 225, and 226 of the robot arms 210 and 220 are moving to subsequent emission points.

However, when the robot arms 210 and 220 include the plurality of link members 211, 212, 215, 216, 221, 222, 225, and 226, radiations may be emitted in a state in which remaining link members are stationary while one of the link members 211, 212, 215, 216, 221, 222, 225, and 226 is moving. Thus, a treatment or surgery time may be reduced.

In addition, when the plurality of robot arms 210 and 220 is provided, the treatment or surgery time may be reduced more efficiently.

Hereinafter, a kinematical analysis on a structure of the medical robot 10 will be described in detail.

The following may be expressed based on forward kinematics.

$$x = f(\theta) \quad \text{[Equation 1]}$$

In the Equation 1, $\theta$ denotes a joint angle, and x denotes a location and direction of an end-effector.

Coordinates of an emitting member may be estimated based on an angle at which link members are connected to each other.

In addition, when a Denavit-Hartenberg (D-H) convention is used, the kinematics of the robot may include four parameters, for example, a link length a of a line member, a link offset d, a link distortion $\alpha$, and a joint angle $\theta$.

In this example, when a joint rotates around a z axis, transformation matrices may be expressed as follows.

$$^0_1T = \begin{bmatrix} c\theta1 & -c\alpha1\ s\theta1 & s\alpha1\ s\theta1 & 0 \\ s\theta1 & c\alpha1\ c\theta1 & -s\alpha1\ c\theta1 & 0 \\ 0 & s\alpha1 & c\alpha1 & R \\ 0 & 0 & 0 & 1 \end{bmatrix} \quad \text{[Transformation Matrix 1]}$$

$$^1_2T = \begin{bmatrix} c\theta2 & -c\alpha2\ s\theta2 & s\alpha2\ s\theta2 & 0 \\ s\theta2 & c\alpha2\ c\theta2 & -s\alpha2\ c\theta2 & 0 \\ 0 & s\alpha2 & c\alpha2 & R \\ 0 & 0 & 0 & 1 \end{bmatrix} \quad \text{[Transformation Matrix 2]}$$

In Transformation Matrices 1 and 2, s denotes sine, and c denotes cosine

Through the above transformation matrices, a transformation matrix may be derived as follows.

$$^0_2T = \begin{bmatrix} c\theta1\ c\theta2 + c\alpha1\ s\theta1\ s\theta2 & s\alpha1\ s\alpha2\ c\theta1 + c\alpha2(c\alpha1\ c\theta2\ c\theta1 + c\theta1\ s\theta2) & c\alpha2\ s\alpha1\ s\theta1 + s\alpha2(c\alpha1\ c\theta2\ c\theta1 + c\theta1\ c\theta2) & 0 \\ c\theta2\ s\theta1 + c\alpha1\ c\theta1\ s\theta2 & -c\theta1\ s\alpha1\ s\alpha2 + c\alpha2(c\alpha1\ c\theta1\ c\theta2 - s\theta1\ s\theta2) & -c\theta1(c\alpha2\ s\alpha1 + c\alpha1\ c\theta2\ s\alpha2) + s\alpha2\ s\theta1\ s\theta2 & 0 \\ s\alpha1\ s\theta2 & c\alpha2\ c\theta2\ s\alpha1 + c\alpha1\ s\alpha2 & c\alpha1\ c\alpha2 - c\theta2\ s\alpha1\ s\alpha2 & R \\ 0 & 0 & 0 & 1 \end{bmatrix} \quad \text{[Transformation Matrix 3]}$$

The above transformation matrix may represent a case in which two link members are provided. A point to which relocation is to be performed by a translation, an offset, a scale, or a rotation on a three-dimensional (3D) coordinate system may be estimated using the transformation matrix.

In addition, a location and direction of the emitting member or the end-effector may be expressed as follows.

$$^0_2T = \begin{bmatrix} ^0x_2 & ^0y_2 & ^0z_2 & ^0p_2 \\ 0 & 0 & 0 & 1 \end{bmatrix} \quad \text{[Transformation Matrix 4]}$$

$$^0p_2 = \begin{bmatrix} 0 \\ 0 \\ R \end{bmatrix} \quad \text{[Transformation Matrix 5]}$$

In this example, the location of the emitting member or the end-effector may be constantly uniform.

Figure 5:
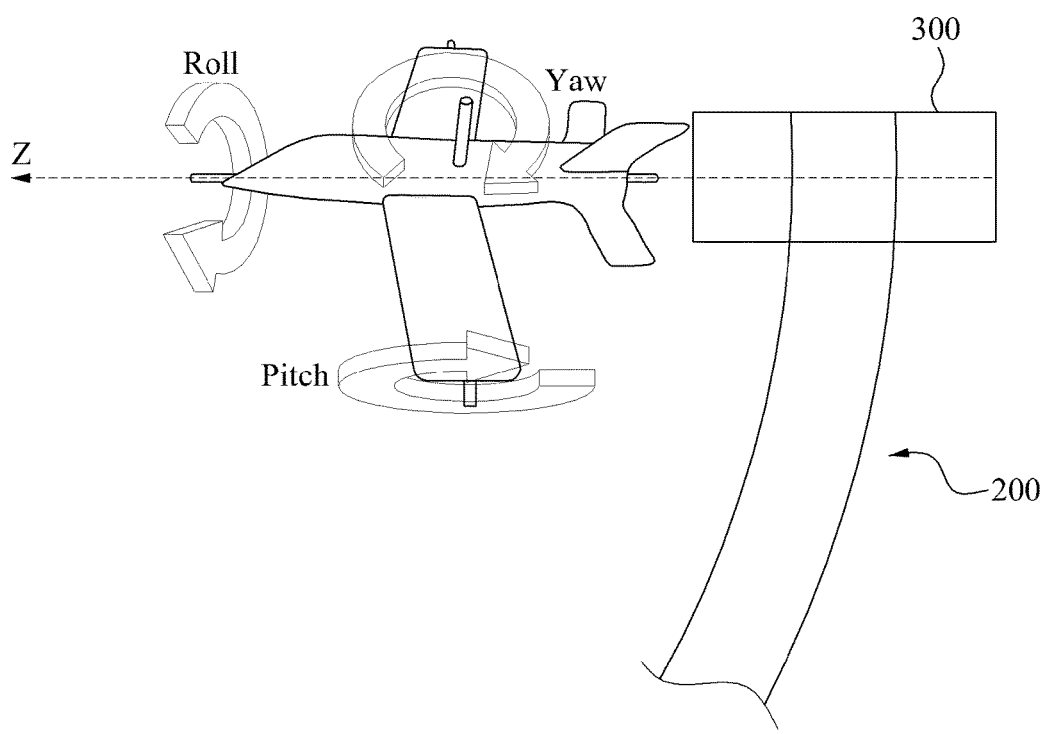
FIG. 5 illustrates a direction of an emitting member in a medical robot according to an embodiment of the present invention.

FIG. 5 illustrates a direction of the emitting member 300 in the medical robot 10.

Referring to FIG. 5, the emitting member 300 may face a z axis, and have a roll movement of rotating on the z axis, a yaw movement of oscillating up and down based on the z axis, and a pitch movement of rotating up and down based on the z axis.

In this example, a roll direction may be insignificant in the emitting member 300. Only a z-vector may be considered for a direction of the emitting member 300. Thus, Transformation Matrix 2 may be arranged as follows.

$$^0z_2 = \begin{bmatrix} z_1 \\ z_2 \\ z_3 \end{bmatrix} = \begin{bmatrix} c\alpha2\ s\alpha1\ s\theta1 + s\alpha2(c\alpha1\ c\theta2\ s\theta1 + c\theta1\ s\theta2) \\ -c\theta1(c\alpha2\ s\alpha1 + c\alpha1\ c\theta2\ s\alpha2) + s\alpha2\ s\theta1 s\theta2 \\ c\alpha1\ c\alpha2 - c\theta2\ s\alpha1\ s\alpha2 \end{bmatrix} \quad \text{[Transformation Matrix 6]}$$

Figure 6:
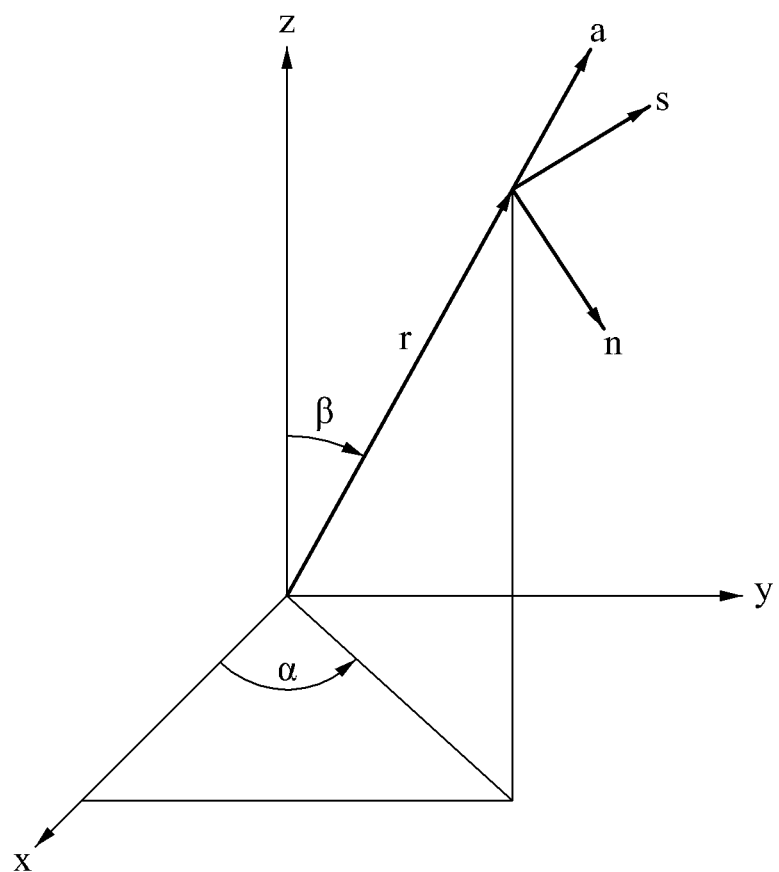
FIG. 6 illustrates spherical coordinates.

A desired direction of the emitting member 300 may be designated as spherical coordinates $\alpha$ and $\beta$ of FIG. 6. When the direction of the emitting member 300 is given as $\alpha$ and $\beta$ of FIG. 6, rotation matrices corresponding to the direction may be expressed as follows.

$$R_{spherical} = R_{z,\alpha} R_{y,\beta} = \begin{bmatrix} c\alpha\ c\beta & -s\alpha & c\alpha\ s\beta \\ s\alpha\ c\beta & c\alpha & s\alpha\ s\beta \\ -s\beta & 0 & c\beta \end{bmatrix} \quad \text{[Rotation Matrix 1]}$$

-continued $$R_{spherical} = \begin{bmatrix} x_1 & y_1 & z_1 \\ x_2 & y_2 & z_2 \\ x_3 & y_3 & z_3 \end{bmatrix}$$ [Rotation Matrix 2]

Based on $\alpha$ and $\beta$ from Rotation Matrices 1 and 2, $^0x_2=[x_1, x_2, x_3]^T$, $^0y_2=[y_1, y_2, y_3]^T$, and $^0z_2=[z_1, z_2, z_3]^T$ may be determined, and $\theta_1$ and $\theta_2$ may also be determined.

Such a relationship may be expressed by inverse kinematics as follows.

$$\theta = f(x)^{-1}$$ [Equation 2]

In Equation 2, x denotes a vector $^0z_2=[z_1, z_2, z_3]^T$ and, $\theta$ denotes a vector including $\theta_1$ and $\theta_2$. Equation 2 may be an inverse function of Equation 1.

The joints angles $\theta_1$ and $\theta_2$ may be calculated based on orthonormal vectors $^0x_2$, $^0y_2$, and $^0z_2$. An intuitive method of calculating such vectors may be performed using spherical coordinates. When a direction is given as $\alpha$ and $\beta$, a rotation matrix corresponding to the direction may be expressed as follows.

$$R_{spherical} = R_{z,\alpha}R_{y,\beta} = \begin{bmatrix} c\alpha\,c\beta & -s\alpha & c\alpha\,s\beta \\ s\alpha\,c\beta & c\alpha & s\alpha\,s\beta \\ -s\beta & 0 & c\beta \end{bmatrix}$$ [Rotation Matrix 3]

In this example, constituent elements of the vectors may correspond to $^0x_2=[x_1, x_2, x_3]^T$, $^0y_2=[y_1, y_2, y_3]^T$, and $^0z_2=[z_1, z_2, z_3]^T$.

The following Equations may be extracted from Transformation Matrix 3.

$$x_3 = s\alpha_1 s\theta_2$$

$$z_3 = c\alpha_1 c\alpha_2 - c\theta_2 s\alpha_1 s\alpha_2$$ [Equation 3]

In Equation 3, $\theta_2$ may be induced as follows.

$$s\theta_2 = x_3 - s\alpha_1$$ [Equation 4]
$$c\theta_2 = \frac{z_3 + c\alpha_1 c\alpha_2}{s\alpha_1 s\alpha_2}$$
$$\tan\theta_2 = \frac{s\alpha_1 s\alpha_2(x_3 - s\alpha_1)}{z_3 + c\alpha_1 c\alpha_2}$$
$$\theta_2 = \arctan2\left(x_3 - s\alpha_1, \frac{z_3 + c\alpha_1 c\alpha_2}{s\alpha_1 s\alpha_2}\right)$$

A function arctan 2, an arctangent function including two input variables, may be used due to a stability of being close to zero input values and a characteristic of a final angle returning to an appropriate quadrant.

$\theta_1$ may be calculated as follows.

The following Equations 5 through 7 may be obtained from Transformation Matrix 4.

$$(x_2 = c\theta_2 s\theta_1 + c\alpha_1 c\theta_1 s\theta_2)c\alpha_1 s\theta_2$$ [Equation 5]
$$(x_1 = -s\theta_1 c\alpha_1 s\theta_2 + c\theta_1 c\theta_2)c\theta_2$$

$$c\alpha_1 s\theta_2 x_2 + c\theta_2 x_1 = c^2\alpha_1 s^2\theta_2 c\theta_1 + c^2\theta_2 c\theta_1$$ [Equation 6]
$$c\theta_1 = \frac{c\alpha_1 s\theta_2 x_2 + c\theta_2 x_1}{c_1^\alpha s^2\theta_2 + c^2\theta_2}$$

$$z_1 = (c\alpha_2 s\alpha_1 + s\alpha_2 c\alpha_1 c\theta_2)s\theta_1 + s\alpha_2 s\theta_2 c\theta_1$$ [Equation 7]
$$z_2 = -(c\alpha_2 s\alpha_1 + s\alpha_2 c\alpha_1 c\theta_2)c\theta_1 + s\alpha_2 s\theta_2 s\theta_1$$

In addition, the following may be assumed.

$$a = c\alpha_2 s\alpha_1 + s\alpha_2 c\alpha_1$$

$$b = s\alpha_2 s\theta_2$$ [Equation 8]

Through Equations 7 and 8, the following may be calculated.

$$a(z_1 = as\theta_1 + bc\theta_1)$$ [Equation 9]
$$b(z_2 = -ac\theta_1 + bs\theta_1)$$
$$az_1 = a^2 s\theta_1 + abc\theta_1$$
$$bz_2 = b^2 s\theta_1 - abc\theta_1$$
$$az_1 + bz_2 = (a^2 + b^2)s\theta_1$$
$$s\theta_1 = \frac{az_2 + bz_2}{a^2 + b^2}$$

Through Equations 6 and 9, $\theta_1$ may be calculated as follows.

$$\theta_1 = \arctan2\left(\frac{az_1 + bz_2}{a^2 + b^2}, \frac{c\alpha_1 s\theta_2 x_2 + c\theta_2 x_1}{c^2\alpha_1 s^2\theta_2 + c^2\theta_2}\right)$$ [Equation 10]

From Equations 4 and 10, the two joint angles $\theta_1$ and $\theta_2$ may be determined. A Jacobian matrix will be described hereinafter. A linear mapping between a $\theta$-space and an x-space may be as follows. Equation 1 may be differentiated as follows.

$$^0\dot{x} = {}^0J\dot{\theta}$$ [Jacobian Matrix 1]

$$^0J = \begin{bmatrix} {}^0z_0 \times ({}^0p_n - {}^0p_0) & {}^0z_1 \times ({}^0p_n - {}^0p_1) \\ {}^0z_0 & {}^0z_1 \end{bmatrix}$$

The Transformation Matrix 1 may be expressed as follows.

$$^0_1T = \begin{bmatrix} {}^0x_1 & {}^0y_1 & {}^0z_1 & {}^0p_1 \\ 0 & 0 & 0 & 1 \end{bmatrix} =$$ [Rotation Matrix 7]

$$\begin{bmatrix} c\theta 1 & -c\alpha 1\,s\theta 1 & s\alpha 1\,s\theta 1 & 0 \\ s\theta 1 & c\alpha 1\,c\theta 1 & -s\alpha 1\,c\theta 1 & 0 \\ 0 & s\alpha 1 & c\alpha 1 & R \\ 0 & 0 & 0 & 1 \end{bmatrix}$$

Thus, the Jacobian matrix may be expressed as follows.

[Jacobian Matrix 2]

$$^0J = \begin{bmatrix} \begin{bmatrix} 0 \\ 0 \\ 1 \end{bmatrix} \times \begin{pmatrix} \begin{bmatrix} 0 \\ 0 \\ R \end{bmatrix} - \begin{bmatrix} 0 \\ 0 \\ 0 \end{bmatrix} \end{pmatrix} & \begin{bmatrix} s\alpha 1\ s\theta 1 \\ -s\alpha 1\ c\theta 1 \\ c\alpha 1 \end{bmatrix} \times \begin{pmatrix} \begin{bmatrix} 0 \\ 0 \\ R \end{bmatrix} - \begin{bmatrix} 0 \\ 0 \\ R \end{bmatrix} \end{pmatrix} \\ \begin{bmatrix} 0 \\ 0 \\ 1 \end{bmatrix} & \begin{bmatrix} s\alpha 1\ s\theta 1 \\ -s\alpha 1\ c\theta 1 \\ c\alpha 1 \end{bmatrix} \end{bmatrix}$$

[Jacobian Matrix 3]

$$^0J = \begin{bmatrix} ^0z_0 \times (^0p_n - {}^0p_0) & ^0z_1 \times (^0p_n - {}^0p_1) \\ ^0z_0 & ^0z_1 \end{bmatrix}$$

$$= \begin{bmatrix} \begin{bmatrix} 0 \\ 0 \\ 1 \end{bmatrix} \times \begin{pmatrix} \begin{bmatrix} 0 \\ 0 \\ R \end{bmatrix} - \begin{bmatrix} 0 \\ 0 \\ 0 \end{bmatrix} \end{pmatrix} & \begin{bmatrix} s\alpha 1\ s\theta 1 \\ -s\alpha 1\ c\theta 1 \\ c\alpha 1 \end{bmatrix} \times \begin{pmatrix} \begin{bmatrix} 0 \\ 0 \\ R \end{bmatrix} - \begin{bmatrix} 0 \\ 0 \\ R \end{bmatrix} \end{pmatrix} \\ \begin{bmatrix} 0 \\ 0 \\ 1 \end{bmatrix} & \begin{bmatrix} s\alpha 1\ s\theta 1 \\ -s\alpha 1\ c\theta 1 \\ c\alpha 1 \end{bmatrix} \end{bmatrix}$$

$$= \begin{bmatrix} \begin{bmatrix} 0 \\ 0 \\ 0 \end{bmatrix} & \begin{bmatrix} 0 \\ 0 \\ 0 \end{bmatrix} \\ \begin{bmatrix} 0 \\ 0 \\ 1 \end{bmatrix} & \begin{bmatrix} s\alpha 1\ s\theta 1 \\ -s\alpha 1\ c\theta 1 \\ c\alpha 1 \end{bmatrix} \end{bmatrix}$$

Thus, the Jacobian matrix may be expressed as follows.

[Jacobian Matrix 4]

$$J = \begin{bmatrix} 0 & s\alpha 1\ s\theta 1 \\ 0 & -s\alpha 1\ c\theta 1 \\ 1 & c\alpha 1 \end{bmatrix}$$

Through Jacobian Matrix 4, when only an angular velocity is considered and a translational velocity is not considered, a singularity may not be achieved except for a case in which $\alpha = n\pi$ and $n \in N$ are satisfied.

As described above, a relationship between a motion of a link member and a motion of an emitting member may be expressed through a Jacobian matrix.

In detail, a location of the emitting member may be estimated based on a current location of a link member. Conversely, to enable the emitting member to face a central point or a target, an operation of a link member may be controlled based on a current location of the emitting member.

Furthermore, when a plurality of robot arms is provided, the plurality of robot arms may be controlled to operate collaboratively through a Jacobian matrix.

According to embodiments, a medical robot may be aimed at a target point rapidly and accurately through relative movements of a robot arm unit and a bed. The medical robot may increase directivity with respect to the target point through easy control, thereby reducing a treatment or surgery time. The medical robot may reduce an overall weight by reducing a number of drive members through a compact design. The medical robot may include separate robot arm units which may be detached or added as necessary, thereby increasing or decreasing a degree of freedom and achieving a flexible design.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A medical robot comprising:
   a bed on which an object is to be disposed;
   a robot arm unit comprising:
   an upper robot arm to rotate above the bed,
   wherein the upper robot arm comprises a plurality of link members and a plurality of drive members, wherein the plurality of link members are disposed on concentric spheres having an identical center, and wherein extension lines of axes of the plurality of drive members are positioned at the identical center,
   a lower robot arm to rotate below the bed,
   wherein the lower robot arm comprises a plurality of link members and a plurality of drive members, wherein the plurality of link members are disposed on concentric spheres having the identical center, and wherein extension lines of axes of the plurality of drive members are positioned at the identical center,
   a first emitting member movable within a trajectory on a sphere having a center at which a target point is disposed,
   wherein one of the upper robot arm and the lower robot arm comprises the first emitting member and the other of the upper robot arm and the lower robot arm comprises a second emitting member; and
   a position adjustment element to adjust a position of the bed,
   wherein the bed and the robot arm unit move relatively in a vertical or horizontal direction, and
   wherein the object is repositioned to the target point by relatively moving the bed and the robot arm unit in the vertical or horizontal direction, and the first emitting member moves to face the target point.

2. The medical robot of claim 1, wherein the first emitting member and the second emitting member are disposed to face an identical target point.

3. The medical robot of claim 1, wherein the upper robot arm and the lower robot arm are disposed within trajectories on spheres having an identical center.

4. The medical robot of claim 1, wherein the identical center of the concentric spheres matches the target point.

5. The medical robot of claim 1, wherein the upper robot arm further comprises:
   a first central member;
   wherein a first link member of the plurality of link members of the upper robot arm rotates on a longitudinal axis of the first central member;
   wherein a first drive member of the plurality of drive members of the upper robot arm is disposed at one end of the first link member to transmit a torque to the first link member;
   wherein a second link member of the plurality of link members of the upper robot arm is connected to another end of the first link member to rotate on a first axis; and
   wherein a second drive member of the plurality of drive members of the upper robot arm is disposed between the first link member and the second link member to transmit a torque to the second link member.

6. The medical robot of claim 5, wherein:
a third link member of the plurality of link members of the upper robot arm is connected to a portion of the first central member, the portion differing from a portion to which the first link member is connected, to rotate on the longitudinal axis of the first central member;
a third drive member of the plurality of drive members of the upper robot arm is disposed at one end of the third link member to transmit a torque to the third link member;
a fourth link member of the plurality of link members of the upper robot arm is connected to another end of the third link member to rotate on a second axis; and
a fourth drive member of the plurality of drive members of the upper robot arm is disposed between the third link member and the fourth link member to transmit a torque to the fourth link member.

7. The medical robot of claim 6, wherein the lower robot arm further comprises:
a second central member;
wherein the second central member is disposed on an axis identical to the longitudinal axis of the first central member and spaced apart from the identical center by a distance corresponding to a distance between the first central member and the identical center;
wherein a fifth link member of the plurality of link members of the lower robot arm rotates on a longitudinal axis of the second central member;
wherein a fifth drive member of the plurality of drive members of the lower robot arm is disposed at one end of the fifth link member to transmit a torque to the fifth link member;
wherein a sixth link member of the plurality of link members of the lower robot arm is connected to another end of the fifth link member to rotate on a third axis; and
wherein a sixth drive member of the plurality of drive members of the lower robot arm is disposed between the fifth link member and the sixth link member to transmit a torque to the sixth link member.

8. The medical robot of claim 7, wherein:
a seventh link member of the plurality of link members of the lower robot arm is connected to a portion of the second central member, the portion differing from a portion to which the fifth link member is connected, to rotate on the longitudinal axis of the second central member;
a seventh drive member of the plurality of drive members of the lower robot arm is disposed at one end of the seventh link member to transmit a torque to the seventh link member;
an eighth link member of the plurality of link members of the lower robot arm is connected to another end of the seventh link member to rotate on a fourth axis; and
an eighth drive member of the plurality of drive members of the lower robot arm is disposed between the seventh link member and the eighth link member to transmit a torque to the eighth link member.

9. The medical robot of claim 8, wherein the longitudinal axis of the first central member, the longitudinal axis of the second central member, the first axis, the second axis, the third axis, and the fourth axis are positioned at the identical center.

10. The medical robot of claim 8, wherein the first axis, the second axis, the third axis, and the fourth axis are formed to be perpendicular to tangential directions of end portions of the first link member, the second link member, the third link member, the fourth link member, the fifth link member, the sixth link member, the seventh link member, and the eighth link member.

11. The medical robot of claim 8, wherein, when the seventh link member is disposed between the fifth link member and the sixth link member, lengths of the seventh link member and the eighth link member are shorter than a length of the fifth link member.

12. The medical robot of claim 11, wherein the seventh link member and the eighth link member are disposed closer to the identical center than the sixth link member, and the eighth link member is disposed closer to the identical center than the seventh link member.

13. The medical robot of claim 8, wherein the first emitting member is provided at an end portion of the second link member or an end portion of the fourth link member, and the second emitting member is provided at an end portion of the sixth link member or an end portion of the eighth link member.

14. The medical robot of claim 13, wherein the first emitting member is disposed to be perpendicular to tangential directions of the end portion of the second link member or the end portion of the fourth link member, the second emitting member is disposed to be perpendicular to tangential directions of the end portion of the sixth link member or the end portion of the eighth link member.

15. The medical robot of claim 7, wherein the first link member and the second link member are disposed farther away from the identical center than the third link member and the fourth link member, and the fifth link member and the sixth link member are disposed farther away from the identical center than the seventh link member and the eighth link member.

16. The medical robot of claim 6, wherein, when the third link member is disposed between the first link member and the second link member, lengths of the third link member and the fourth link member are shorter than a length of the first link member.

17. The medical robot of claim 16, wherein the third link member and the fourth link member are disposed closer to the identical center than the second link member, and the fourth link member is disposed closer to the identical center than the third link member.

* * * * *